(12) United States Patent
Tatarek et al.

(10) Patent No.: US 8,517,021 B2
(45) Date of Patent: Aug. 27, 2013

(54) VACUUM DEMAND VALVE

(75) Inventors: Andrew Richard Thomas Tatarek, Aldershot (GB); Gunther Weiszl, Wiener Neudorf (AT)

(73) Assignee: Linde Aktiengesellschaft, Munich (DE)

( * ) Notice: Subject to any disclaimer, the term of this patent is extended or adjusted under 35 U.S.C. 154(b) by 493 days.

(21) Appl. No.: 12/893,062

(22) Filed: Sep. 29, 2010

(65) Prior Publication Data

US 2011/0240028 A1 Oct. 6, 2011

(51) Int. Cl.
*A62B 9/00* (2006.01)
*A61M 16/20* (2006.01)
*F16K 31/126* (2006.01)

(52) U.S. Cl.
USPC ............ 128/205.24; 128/204.26; 128/205.12; 128/205.19; 128/207.12; 128/910; 137/115; 137/14; 137/115.18; 251/901

(58) Field of Classification Search
USPC ............. 128/200.27, 201.28, 203.13, 204.18, 128/204.26, 205.12, 205.19, 205.24, 207.12, 128/910; 137/115.14, 115.18, 908; 251/901
See application file for complete search history.

(56) References Cited

U.S. PATENT DOCUMENTS

| 3,604,448 A | | 9/1971 | Marrese et al. | |
|---|---|---|---|---|
| 3,800,793 A | * | 4/1974 | Marrese et al. | 128/203.12 |
| 3,951,168 A | * | 4/1976 | Roberts | 137/625.28 |
| 4,109,651 A | | 8/1978 | Steigerwald | |
| 4,291,689 A | * | 9/1981 | Hay | 128/200.24 |
| 4,411,285 A | * | 10/1983 | Oswell | 137/112 |
| 4,643,214 A | * | 2/1987 | Blumenthal | 137/12 |
| 6,305,375 B1 | * | 10/2001 | Brown | 128/205.24 |
| 6,772,785 B2 | * | 8/2004 | Jackson | 137/489 |

FOREIGN PATENT DOCUMENTS

| CN | 2642338 Y | 9/2004 |
|---|---|---|
| EP | 0 051 045 A1 | 5/1982 |
| EP | 0 375 939 A2 | 7/1990 |
| FR | 2395036 A | 1/1979 |
| GB | 2 178 325 A | 2/1987 |
| WO | WO 2008/101302 A1 | 8/2008 |

* cited by examiner

*Primary Examiner* — Justine Yu
*Assistant Examiner* — Timothy Stanis
(74) *Attorney, Agent, or Firm* — David A. Hey (57) ABSTRACT

A vacuum demand valve for controlling flow of exhalation gases from a patient to a vacuum line. The demand valve comprises: a housing having a housing inlet that allows exhalation gases to flow into the housing from a patient, and a housing outlet that allows gases to flow from the housing into the vacuum line; a diaphragm having a flexible skirt and a rigid portion moveable in response to gas pressure in the housing; a sealing member connected to the rigid portion to engage the housing outlet to resist the flow of gases from the housing to the vacuum line. In a first condition, the vacuum line pressure causes the sealing member to engage the housing outlet and in a second condition a predetermined pressure of exhalation gases in the housing causes the sealing member to disengage from the housing outlet.

12 Claims, 7 Drawing Sheets

VACUUM DEMAND VALVE

CROSS REFERENCE TO RELATED APPLICATIONS

This application claims priority from United Kingdom Patent Application Serial No. GB0916971.5 filed Sep. 29, 2009.

FIELD OF INVENTION

The present invention relates to a vacuum demand valve for use on the exhalation side of a breathing apparatus for controlling the flow of exhalation gases from a patient to a vacuum line, for example, a vacuum line connected to a vacuum source of a hospital waste gas disposal system.

BACKGROUND OF THE INVENTION

In hospitals and surgeries, where a range of anaesthetic gases are used, there is a problem in dealing with the exhaled gas, such as $N_2O$. Not all inhaled anaesthetic gas is absorbed by the patient, and it is undesirable for the clinicians in the area to inhale the gases. Although the levels are low, long term exposure may present potential health hazards. Existing prior art scavengers are designed to dispose exhaled gases without allowing them to vent to atmosphere.

In one prior art system disclosed in U.S. Pat. No. 4,527,558, the gas scavenger system includes an exhalation line that transmits exhalation gases from a patient to a surge chamber prior to eventual discharge into a vacuum system. The surge chamber provides an interface between the vacuum system and a collection manifold and is connected to the vacuum system through a predetermined sized orifice which limits the flow to the vacuum system to a maximum known flow. The surge chamber normally allows continuous flow through the orifice to the vacuum system but acts as a buffer and is sized to accumulate the volume of any exhaled flow that exceeds the continuous flow during a breathing cycle, including an excess of flow from the collection manifold under abnormal conditions such as is occasioned at a large exhalation or when a patient coughs. Therefore, the surge chamber allows time to remove the gases through the orifice and thus to prevent leakage to atmosphere. While the patient is exhaling, the exhaled gas that was not drawn into the vacuum system is drawn out from the surge chamber. As long as the surge chamber is bigger than the largest exhalation anticipated and the average exhaled flow is smaller than the constant flow, the system will prevent the exhaled gas entering the surroundings. The surge chamber itself is directly connected to atmosphere through a known, fixed resistance such that an excess in pressure in the surge chamber above that determined by the known fixed resistance is bled to atmosphere. Thus, in the event of an occlusion in the vacuum line, the patient is assured a path for exhalation. Also, in the event the vacuum system draws gas at a faster flow rate than that of waste gases entering the surge chamber from the collection manifold, gas will be drawn from atmosphere through the known, fixed resistance. The pressure is thus controlled at the collection chamber to prevent an excess of either pressure or vacuum from affecting the function of a normal demand valve or breathing apparatus supplying the anaesthetic containing gas.

In a scavenging system, all of a patient's exhalation gases should be transferred to the hospital vacuum system. The resistance to exhalation should be small, to make it comfortable for the patient, and to help achieve evacuation of exhaled gases. The patient should not be able to re-breathe exhalation gases that have already been exhaled into the scavenger. The patient should be protected from vacuum flow. The patient should still be able to exhale in the event of failure of the vacuum or it being weak. A clinician should be able to see that the scavenger is operating properly.

In the prior art system, a constant vacuum flow is drawn regardless of patient exhalation. Thus, the device may use significantly more vacuum flow than needed for the patient, wasting valuable energy and causing a drain on the hospital vacuum system. If the vacuum flow is adjusted so that it is lower, to conserve energy, some of the patient's exhaled breath may well escape to atmosphere.

The prior art systems must be turned on and off prior to and after use. That is, the vacuum connection to the device needs to be turned on and off. If a user forgets to turn the device on, then a patient may inadvertently exhale to atmosphere. If a user forgets to turn off the device after use, there will be a constant drain on the hospital vacuum system. There is also a need to adjust vacuum flow for the breathing cycle of different patients, due to, for example, size, fitness and age of a patient. In this regard, the prior art devices may have an adjustment to make the constant flow higher or lower according to patient size, necessitating yet another aspect which must be controlled by a clinician, requiring some prior judgment in order to make an adjustment.

The size of the surge chamber has to be larger than the maximum tidal volume (the largest amount that may be exhaled in one breath) of the largest patient liable to be encountered. Therefore, the surge chamber must be relatively large having a capacity in the region of 2-5 liters or around 500 mm tall and 100 mm diameter, with a weight in the region of 1 to 5 kg. This means that the scavenger is large relative to typical medical equipment such as a demand valve or a gas mixer and therefore it may occupy an undue amount of space, and be inconvenient to move. Further, the size of the device and the amount of material used in its manufacture will result in a high cost high, even though the technology may be simple.

The constant flow of air into the vacuum system can cause a background noise, where the surge chamber can act as a sounding device, amplifying the sound, which can be a strain on the user and the patient. Further, there is very limited indication that the scavenger is operating properly, as there are no moving parts to be observed.

SUMMARY OF THE INVENTION

The present invention provides a vacuum demand, or diaphragm, valve for use on the exhalation side of a breathing apparatus for controlling the flow of exhalation gases from a patient to a vacuum line, the demand valve comprising:

a housing having a housing inlet which can be connected to an exhalation line of a breathing apparatus to allow exhalation gases to flow into the housing from a patient and a housing outlet which can be connected to a vacuum line to allow gases to flow from the housing into the vacuum line;

a diaphragm having a flexible skirt connected to the housing and a rigid portion supported by the flexible skirt and moveable in response to gas pressure in the housing due to fluctuations in exhalation flow; and a sealing member connected to the rigid portion of the diaphragm which can engage with the housing outlet to resist the flow of gases from the housing to the vacuum line;

wherein in a first condition of the diaphragm, the pressure in the vacuum line causes the sealing member to engage the housing outlet for resisting flow of gases from the housing to the vacuum line and in a second condition of the diaphragm a positive predetermined pressure of exhalation gases in the housing acts on the rigid portion of the diaphragm causing the sealing member to disengage at least partially from the housing outlet allowing exhalation gases to flow from the housing to the vacuum line and wherein, the sealing member may comprise a flexible sealing portion which in the first condition of the diaphragm closes the housing outlet and when pressure in the housing increases above the predetermined pressure due to exhalation, the diaphragm disengages the sealing portion by rolling the sealing portion to open progressively the housing outlet.

In normal operating conditions the diaphragm may remain in the first condition with the housing outlet sealed by the sealing member unless exhalation gas pressure acting on the rigid portion is sufficient to move the diaphragm into the second condition so that the demand valve closes vacuum flow into the vacuum line unless the demand valve is connected to an exhalation line of a breathing apparatus and the apparatus is in use.

Movement of the diaphragm may be proportional to the flow of exhalation gases flowing into the housing so that the amount by which the housing outlet is progressively opened is dependent on the amount of exhalation by a patient.

The housing outlet may comprise a seat having a plurality of openings therethrough for the flow of gas from the housing to the vacuum line. In this case, the sealing portion of the sealing member may be formed by a membrane and the seat supports the membrane between the openings and/or the sealing portion comprises strengthening ribs for supporting the membrane.

The rigid portion of the diaphragm may comprise a plurality of openings therethrough to allow the flow of gas between the housing and atmosphere and the demand valve may comprise a valve for selectively sealing the openings in normal operative conditions of the demand valve or opening the openings in adverse operative conditions of the demand valve. In this regard, adverse operating conditions may comprise a reduction in vacuum pressure in the vacuum line such that vacuum flow into the vacuum line is not sufficient to suck away the exhalation gases in the housing, and wherein the valve opens the openings in the diaphragm to allow exhalation gases to flow to atmosphere. One or both of the housing and the valve may comprise projections which engage with the other of the housing and the valve for opening the openings in the diaphragm when the pressure in the housing increases above an upper limit pressure so that exhalation gases can be exhausted to atmosphere from the housing.

Adverse operating conditions may alternatively or additionally comprise the sealing member ineffectively sealing the housing opening such that a vacuum flow occurs from the housing to the vacuum line when the diaphragm is in the first condition, and wherein the valve opens the openings in the diaphragm to allow the flow of gas from atmosphere into the housing.

The housing may comprise a wall which surrounds the housing outlet and when the pressure in the housing is reduced below a lower limit pressure, the diaphragm moves to engage the wall thereby substantially sealing the housing inlet from the housing outlet.

At least a portion of the housing may be made from a transparent material so that movement of the diaphragm in use can be observed through the housing.

The housing inlet may comprise a one way-valve for resisting the flow of exhalation gases from the housing to the exhalation line.

It will be understood that a patient has a breathing cycle comprising an inhalation stage and an exhalation stage, and wherein the diaphragm is preferably sized such that the predetermined pressure in the housing at which the sealing member opens the housing outlet is exceeded only a short time after the commencement of the exhalation stage to avoid significant resistance to exhalation being applied to the patient by the demand valve.

BRIEF DESCRIPTION OF THE DRAWINGS

In order that the present invention may be well understood, embodiments thereof, which are given by way of example only, will now be described with reference to the accompanying drawings in which.

The first and second valves are shown in FIGS. 1 and 2a and b, respectively, for purposes of explaining the invention.

DETAILED DESCRIPTION OF THE INVENTION

Figure 8:
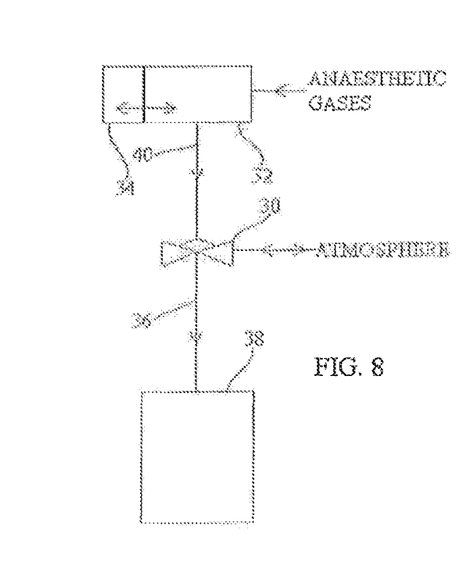
FIG. 8 is a schematic drawing of a breathing apparatus, demand valve and vacuum source.

Referring to FIG. 8, a vacuum demand, or diaphragm, valve 30 is shown for use on the exhalation side of a breathing apparatus 32 for controlling the flow of exhalation gases from a patient 34 to a vacuum line 36. Known demand valves are connected to control the supply of compressed gas to a patient rather than to control the supply of exhaled gas to a vacuum.

A typical breathing apparatus may comprise a mask adapted to be placed over a nose and mouth of a patient for allowing a mixture of anaesthetic gases to be breathed in by a patient an exhaled along an exhalation line 40 to the demand valve 30. The vacuum line is connected to a source of vacuum, which is typically a hospital waste gas disposal system 38. Usually a hospital wall or ceiling has a vacuum port to which a vacuum line can be connected from the demand valve to the vacuum source the latter of which is located elsewhere in a hospital. In use of the arrangement shown in FIG. 8, a mixture of anaesthetic gases is introduced to the breathing apparatus 32 in a manner typically controlled by an anaesthetist or from a demand valve for supplying analgesic gas such as 50/50 $N_2O/O_2$. The gases are breathed by the patient and exhaled along exhalation line 40. The demand valve is configured to allow gas flow between the patient and the vacuum line only under prescribed conditions to avoid injury or discomfort to the patient caused by connecting a patient's respiratory system directly to vacuum. As described in more detail below, the demand valve 30 may further be arranged to allow exhalation gases to be exhausted to atmosphere for example if the vacuum line 36 were to lose or partially lose vacuum. Alternatively, the demand valve is arranged to allow atmosphere to be connected to the vacuum line.

Figure 1A:
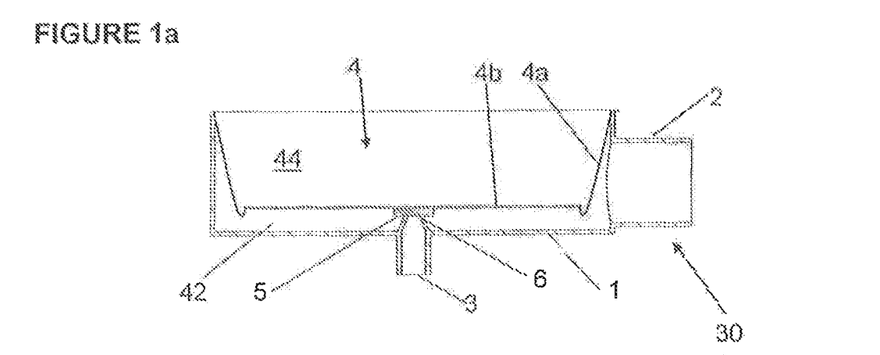
FIGS. 1a and 1b show in section a first demand valve in a first condition in FIG. 1a in which the demand valve is closed and in a second condition in FIG. 1b in which the demand is open.
Figure 1B:
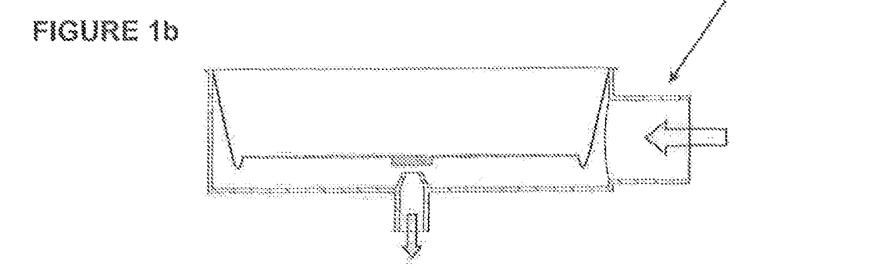

Referring to FIGS. 1a and 1b, the demand valve 30 comprises a first housing part 1 having a housing inlet 2 which can be connected to an exhalation line 40 of a breathing apparatus to allow exhalation gases to flow into the housing from a patient. A housing outlet 3 can be connected to an inlet port of a vacuum line 36 to allow gases to flow from the housing into the vacuum line. The housing comprises a second housing part in the form of a cover (not shown).

Figure 3:
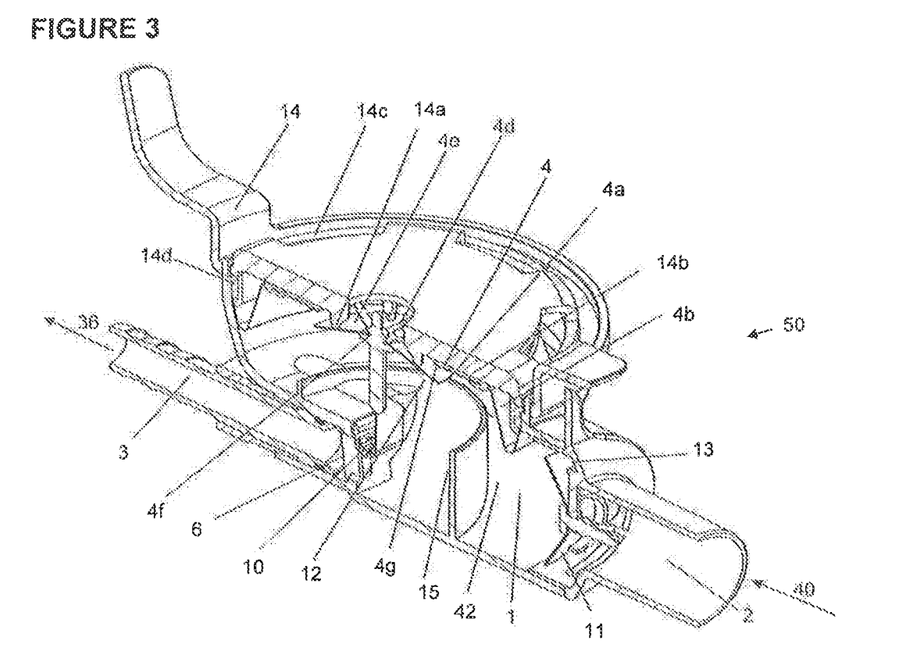
FIG. 3 shows a cut-away of a third demand valve, the third demand valve being in accordance with the invention.

A diaphragm 4 has a flexible skirt 4a connected to the housing and a rigid portion 4b supported by the flexible skirt and moveable in response to gas pressure in the housing, due to exhalation in normal operation of the valve. The flexible skirt may be made from rubber, polyurethane, or similar elastomeric material, and secured to housing by bonding, the outer edge of the diaphragm having a bead of material which can be stretched over the top edge of the body 1, or a bead retained over a grove on a cover, which is then inserted into the top of the body 1, trapping the bead (as can be seen in FIG. 3). The rigid portion may be formed by a stiff generally circular disc made from a metal such as aluminium, or a rigid plastic, such as glass filled nylon. The diaphragm 4 separates the housing into a first region 42 which as shown is below the diaphragm and a second region 44 above the diaphragm. The pressure in the first region 42 is determined by the cyclical fluctuations in the patient's breathing. The pressure is the second region 44 is approximately atmospheric.

The housing outlet comprises a seat 6 having an opening through which gas can flow to the vacuum line. A seal, or sealing member, 5 is connected, or fixed relative, to the rigid portion 4b of the diaphragm. The seal can engage with seat 6 to resist the flow of gases from the housing to the vacuum line 36.

In a first condition of the diaphragm as shown in FIG. 1a, the pressure in the vacuum line causes the seal 5 to engage with the seat 6 for resisting flow of gases from the housing to the vacuum line 36. In a second condition of the diaphragm shown in FIG. 1b, the pressure of exhalation gases from a patient act on the rigid portion 4b of the diaphragm causing the seal 5 to disengage from the housing outlet 3 allowing exhalation gases to flow from the housing to the vacuum line 36. The demand valve is configured so that when a patient exhales, the seal 5 is disengaged from the seat 6 so that the exhalation gases can be exhausted along the vacuum line 36 for disposal. When a patient is not exhaling (i.e. is inhaling or pausing), the seal is engaged with the seat thereby preventing flow connection between the patient and the vacuum line.

There is a balance of forces acting in the demand valve 30. Atmospheric pressure acts in second region 44 of the housing and the net force acting on the seal is determined by the pressure in the first region 42 of the housing relative to atmosphere and the pressure in the vacuum line 36 relative to atmosphere. The pressure in the vacuum line is generally constant but may vary from time to time depending on the vacuum system and the flow of gas through the vacuum line. In typical hospital vacuum systems, the pressure may be in the region of −600 to −1000 mbarg. The pressure in region 42 of the housing varies cyclically during the breathing cycle of a patient. In this latter regard, the pressure in region 42 increases to around +0.5 mbarg when a patient exhales.

The seal is fixed relative to the rigid portion 4b. Therefore, the disengaging force acting on the seal is determined by the pressure in region 42 multiplied by the effective area of the diaphragm over which that pressure acts. The engaging force acting on the seal is determined by the pressure in the vacuum line relative to atmosphere multiplied by the effective area of the seat 6 over which the vacuum acts. The effective area of the diaphragm and the effective area of the seat are selected so that the disengaging force exceeds the engaging force at a predetermined pressure in region 42 during the breathing cycle of a patient. At the predetermined pressure the seal disengages from the seat thereby drawing exhalation gases into the vacuum line from housing 1.

Figure 10:
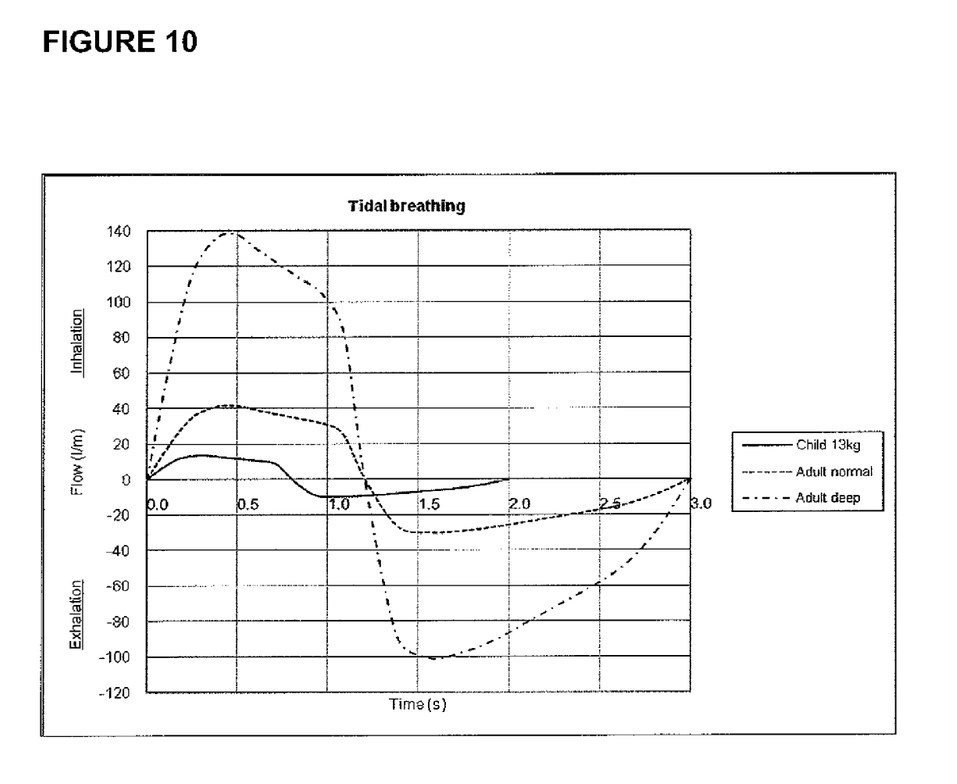
FIG. 10 shows typical tidal breathing for an adult breathing normally, an adult breathing deeply and a child.

It has been found that a desirable predetermined pressure is approximately 0.5 mbar above atmosphere, which can be achieved by an adult patient shortly after an exhalation stage of a breathing cycle begins. FIG. 10 shows a graph of typical breathing cycles for an adult breathing normally, an adult breathing deeply and a child weighing 13 Kg. It will be seen that for an adult breathing normally, the inhalation stage occurs over time 0.0 to 1.2 seconds and the exhalation stage occurs over time 1.2 to 3.0 seconds. When the exhalation stage begins, exhalation gases flow along the exhalation line 40 to the demand valve increasing pressure in the housing. The demand valve is configured so that it opens communication with the vacuum line at a time between 1.2 and about 1.5 seconds so that significant resistance to breathing is not applied by the valve. The valve may require adjustment so that for a child it opens at the appropriate pressure.

Figure 2A:
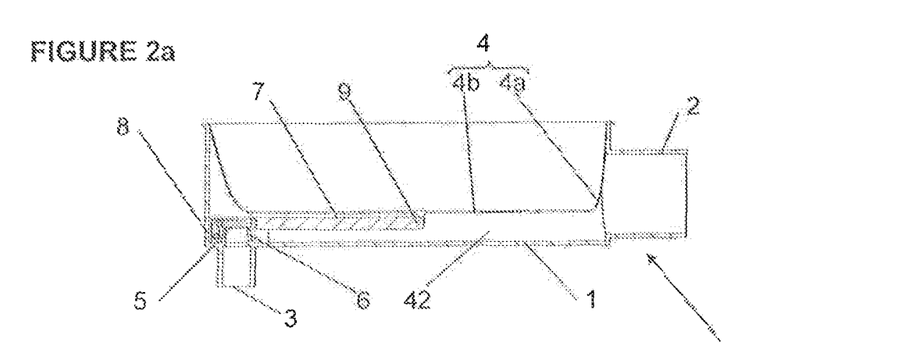
FIGS. 2a and 2b show in section a second demand valve in a first condition in FIG. 2a in which the demand valve is closed and in a second condition in FIG. 2b in which the demand is open.
Figure 2B:
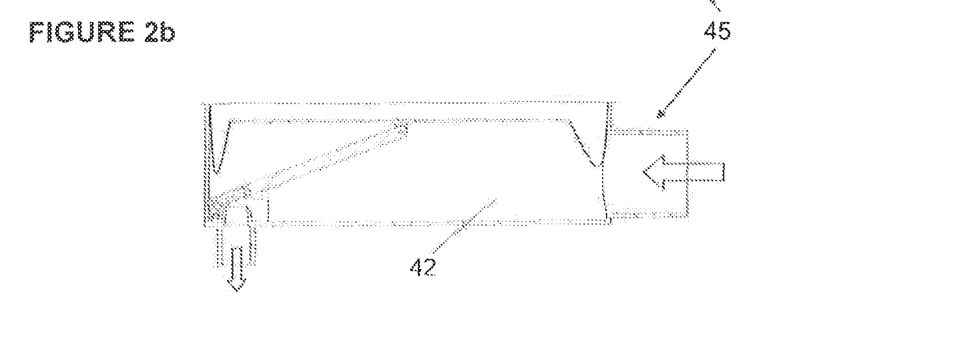

It will be appreciated that relative to atmosphere, the pressure in the vacuum line is many times greater than any possible exhalation pressure of a patient. For example, the vacuum line may be at a pressure of −1000 mbarg whereas the predetermined pressure may be selected to be around +0.5 mbarg (above atmosphere). Accordingly, in order to balance the net forces on the seal 5 at the predetermined pressure, the effective area of the diaphragm must be significantly larger than the effective area of the seat. A large diaphragm increases the size of the demand valve and therefore may not be desirable in some circumstances. FIGS. 2a and 2b show a vacuum demand valve 45 in which the size of the diaphragm is reduced.

FIGS. 2a and 2b will now be described using like reference numbers for like features described in relation to FIGS. 1a and 1b.

In operation and structure, demand valve 45 is similar to demand valve 30 except that a lever arrangement is provided to give a mechanical advantage of greater than 1:1 for increasing the disengaging force which can be applied to the seal 5 by pressure in region 42 of the housing. Accordingly, the size of the diaphragm may be reduced.

FIG. 2a shows a lever arrangement in which the sealing member comprises a lever 7 which is supported for pivotal movement at pivot 8. A first end portion of the lever member is connected by pivot 9 to the rigid portion 4b of the diaphragm. A sealing portion 5 is located at a second end portion of the lever member 7. In this example, the ratio of the distance of the diaphragm connection from pivot 8 to the distance of the seal from the pivot 8 is such as to give a mechanical advantage of about 8:1. In use, the force produce by the pressure in region 42 of the demand valve is five times greater than the force produced in the demand valve of FIGS. 1a and 1b. Accordingly, the effective area of the diaphragm can be reduced by a multiple of five. In practice, it is difficult to achieve a lever ratio of better than 10:1, because, as the demand valve decreases in size, the space for a lever reduces. The table below shows further examples a reduction in effective area of the diaphragm.

| Mechanical advantage | Calculated diaphragm diameter | Real outside diameter of diaphragm, allowing 15 mm for skirt (4a). |
| --- | --- | --- |
| 1 (no advantage per FIGS. 1a & 1b) | 268 | 283 |
| 2 | 190 | 205 |
| 5 | 120 | 135 |
| 10 | 85 | 100 |
| 20 | 60 | 75 |

A further vacuum demand valve 50 is shown in FIGS. 3 to 7. Like reference numbers will be used for like features described in relation to FIGS. 2a and 2b, and 3a and 3b.

A specific advantage of demand valve 50 over the previously described demand valves is that the seat can be opened progressively in response to the changes of pressure due to the breathing cycle of a patient. Accordingly, if a patient exhales more strongly the exhalation pressure produces a larger opening in the seat and conversely, less exhalation induces a smaller opening in the seat. Therefore, the amount of vacuum flow drawn by the valve is purely proportional to the amount required to dispose of the exhalation gases and hence power taken from the vacuum system is reduced. Further, as the seat is opened progressively, less force is required to be generated by the diaphragm to release the seal from the seat, which, in practice gives a bigger effect than the mechanical advantage of a lever. In the previous embodiments, the whole seal is pulled away against the vacuum. In this embodiment, a small part of the seal is pulled away from the diaphragm at any point in opening or closing, reducing the force. Hence, the size of the demand valve can be reduced.

Referring now in detail to FIGS. 3, 3a, 3b and 3c, the demand valve 50 comprises a valve housing 1 having an inlet 2 and outlet 3. The inlet can be connected to an exhaust line 40 of a breathing apparatus 32 so that exhalation gas from a patient 34 can flow into the housing. The outlet can be connected with a vacuum line 36 so that exhalation gases from the patient can be exhausted to a vacuum source 38.

A one-way valve 11 is located at the inlet 2 which opens to allow exhalation gases to enter the housing 1 and closes to resist the flow of gas from the housing 1 to the exhalation line 40. One-way valve 11, as shown in FIG. 3, is a valve flap made from a resilient and flexible material such as rubber or polyurethane and is generally circular and flat. A retaining member projects through a central hole in the flap to secure the central portion of the flap to the housing 1. An outer portion of the flap is free to move and is biased against a seat 13 at the outlet 2 to close the valve. The valve is opened in response to flow of exhalation gases which cause the outer portion of the flap to move away from the seat 13 providing a passage of gases between the valve and the seat. In the absence of flow from the exhalation line the valve is closed due to the internal bias of the valve flap. Accordingly, the valve 11 prevents exhalation gases in the housing from flowing back through exhalation line to be breathed again by the patient.

The outlet 3 comprises a seat 6 having an aperture through which gas can flow from the housing 1 to the vacuum line 36. A seal 10 can engage with the seat 6 for preventing the flow of gas into the vacuum line. The seal 10 is connected so one end is fixed to a diaphragm 4 and an opposing end is fixed to the housing 1. The seal comprises a flexible sealing portion which in one condition of the diaphragm seals the seat and in a second condition of the diaphragm is peeled away from the seat to allow gas to flow through the aperture in the seat.

Figure 3A:
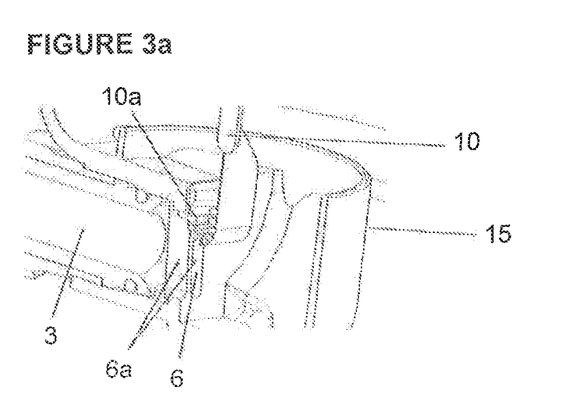
FIGS. 3a, 3b, 3c and 3d show some of the parts of the third demand valve in more detail.
Figure 3B:
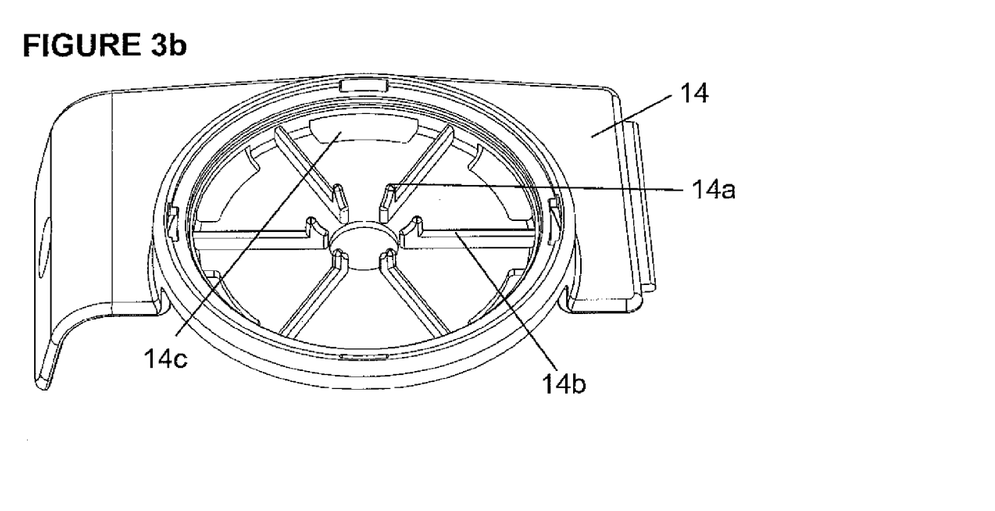
Figure 3C:
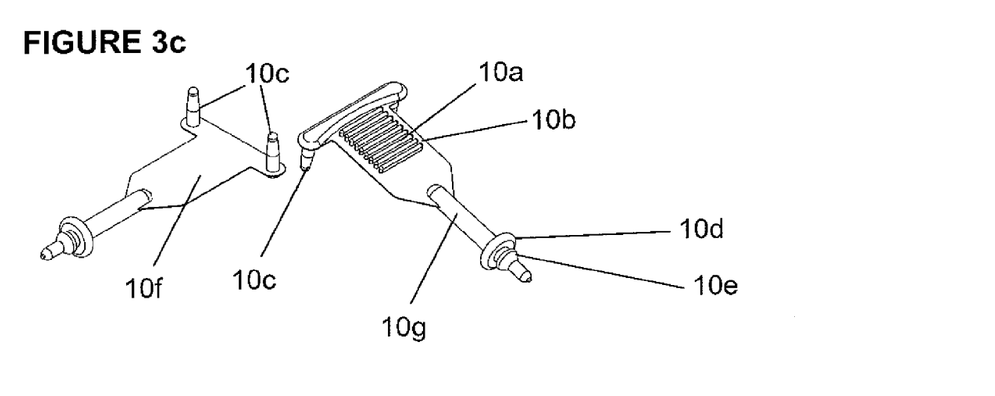

The seal, or rolling seal member, 10 is shown in detail in FIG. 3c. A shaft portion 10g of the seal 10 comprises opposing flanges 10d and 10e which fix the seal to the diaphragm 4. The seal extends through an opening in the rigid portion 4f of diaphragm and the flanges engage on either side of the diaphragm. The flanges 10d and 10e also locate a valve 12 relative to the diaphragm. The valve 12 will be described in greater detail below.

An opposing end portion of the seal 10 comprises two projections 10c which can be press fitted into corresponding bores of slightly smaller diameter than that of the projections 10c in the housing part 1 for fixing the opposing end portion of the seal to the housing. A central portion of the seal 10 is flexible and comprises sealing portion 10f which can seal against the seat 6 or be rolled away to expose the aperture(s) in the seat, as shown in FIG. 3 and in more detail in FIG. 3a.

The sealing portion of the seal may consist of a strip, or membrane, of thin (typically in the region of 0.2 mm thick) flexible resilient material such as silicone rubber or polyurethane. The provision of a sealing film allows a more effective seal to be produced as the membrane is pressed against the seat by the pressure difference across the seat 6. However, a membrane may tend to be sucked into the seat opening by the differential pressure across the membrane, which can cause either puckering at the edges of the membrane causing leakage, or may decrease effective peeling of the seal away from the seat. Accordingly, the opening in the seat may consist of a slot or a plurality of slots, 6a as shown in FIG. 3a. The material of the seat between the slots acts as a support to the membrane, reducing the distance which the seal membrane has to bridge without support from the seat. This arrangement reduces the amount of material which can be sucked into the outlet and therefore reduces leakage and promotes efficient rolling of the membrane.

As shown in FIG. 3a, the generally longitudinal slots 6a provide support for the seal in one direction (vertical as shown). The membrane is supported in a transverse, or horizontal, direction by the provision of ribs 10a extending across a back of the seal portion. The ribs extend in a direction which is perpendicular to movement of the diaphragm to allow the sealing portion to be rolled. The ribs additionally help to control the diameter of the roll generated when the seal is peeled away from the seat.

If ribs are provided, the sealing portion preferably includes an area of material 10b which surrounds the ribs and which engages with an outer periphery of the seat. The area of membrane 10b is readily compressed against the seat by the pressure differential across the seal and sits flush against the seat providing an extended leakage path from the housing to the outlet 3.

Alternatively, in order to support the membrane in perpendicular directions (vertical and horizontal), the seat may comprise a series of small holes, preferably in the form of a grid. The material of the seat between the holes supports the seal membrane in both horizontal and vertical directions, which can remove the need for the ribs, 10a across the membrane.

When exhalation gases enter the housing, a force is exerted by the increased pressure which lifts the diaphragm. Resistance to lifting is provided by the vacuum pressure in the vacuum line acting on the seal 10. For each unit of movement of the diaphragm only a relatively small amount of the seat is opened. When the seat is initially opened, gas can flow through the small opening thereby decreasing the differential pressure between the housing and the vacuum line.

As more or less flow enters the demand valve, the diaphragm moves higher or lower, so that the open area of the seat, and hence the flow from the demand valve into the vacuum line balances the flow into the valve. The pressure in the chamber 42 remains substantially constant during exhalation. Narrower taller apertures in the seal further decrease the required disengaging force, but would require more travel of the diaphragm.

This arrangement gives an effective mechanical advantage which is greater than that possible in the FIG. 2 arrangement and reduces still further the possible reduction in diameter of the diaphragm.

The valve described can be made smaller than any of the designs previously described, and realistically within a diameter of 70 mm, which is of a size that is easy to package, and with parts that are inexpensive to manufacture.

The diaphragm 4 comprises a flexible skirt 4b and a rigid portion 4a. The flexible skirt is fixed at an outer periphery to the housing between housing parts 1 and 14 allowing movement of the rigid portion 4a towards and away from the seat 6 (upwards and downwards as shown in FIG. 3). Cover part 14 may contain suitable means, such as screw holes, clips or other fastening means, for mounting the demand valve 50 to a medical device. Cover 14 has a downwardly projecting flange having an annular groove 14d for receiving the flexible skirt and forming an air-tight connection between the diaphragm and the housing 1. The cover 14 has openings, in the form of segments, 14c (see FIG. 3b) through which gas can flow into the housing from atmosphere or from the housing to atmosphere. The demand valve 50 controls the flow of gas into and out of the housing through openings 14c as will now be described.

The diaphragm 4 has openings 4e allowing the flow of gas therethrough. The openings 4e are formed by segments located at a generally central region of the rigid portion 4a of the diaphragm. A plurality of radially extending connecting portions, or spokes, 4d extend between the segments from a central hub to an outer region of the rigid portion 4g.

A valve 12 is provided for selectively closing the openings 4e in the diaphragm so that gas can flow into or out of the demand valve. The valve 12 is formed by a flap valve having a central opening for receiving the seal member 10 such that the flanges 10d and 10e (see FIG. 3c) fix the valve 12 to the central hub of the diaphragm. The flap is made from a resilient and flexible material such as rubber or polyurethane and is generally circular and flat. The flap has an internal bias which causes it to sit flush against the rigid portion 4g thereby closing the openings 4e in the diaphragm.

The cover part 14 is shown in detail in FIG. 3b. FIG. 3b is a perspective view from beneath the cover part. A plurality of projections 14a project away from the cover and are adapted to extend through openings 4e in the diaphragm and abut against the valve flap 12. If the rigid portion 4f of the diaphragm moves sufficiently towards the cover, the projections 14a cause the flap valve 12 to disengage from the diaphragm allowing gas to flow through openings 4e. Ribs 14b are provided on the cover in order to space the rigid portion 4a of the diaphragm from the cover to allow gas to flow between the cover and the diaphragm, and through the openings 14c in the cover. When the rigid portion 4a moves away from the cover, the valve flap 12 moves under its internal bias to cover the openings 4e and prevent the flow of gas.

Figure 3D:
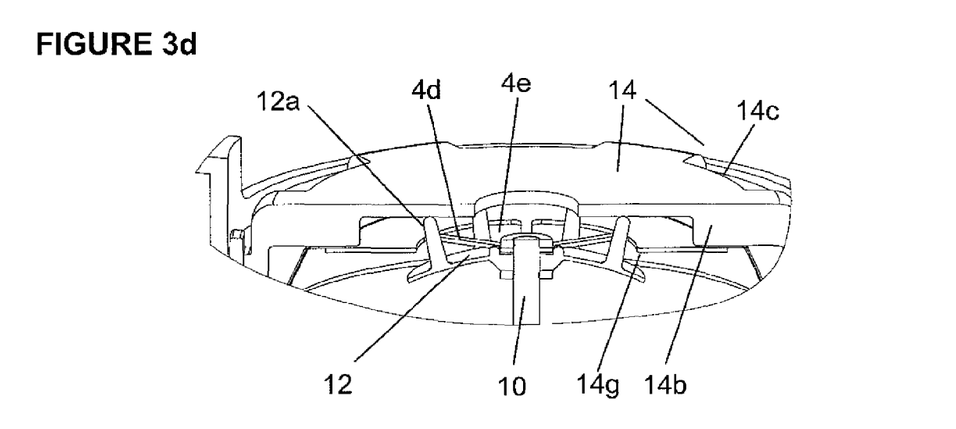

FIG. 3d shows an alternative arrangement in which valve flap 12 comprises upstanding projections which are adapted to engage the cover part 14 for spacing an outer portion of the flap from the diaphragm when the diaphragm has moved to its upper extent of movement.

The housing part 1 comprises a wall 15 which surrounds the seat 6. When the pressure in the housing is reduced by continued exposure of the housing to the vacuum line, the rigid portion 4a of the diaphragm is moved downwards until it engages the wall 15 thereby substantially sealing the region 42 of the housing from the region 52 of the housing and accordingly, substantially sealing the inlet 2 from the outlet 3.

Use of the demand valve 50 will now be described with reference to FIGS. 4 to 6 and 7, which show four operative states of the demand valve.

Figure 4:
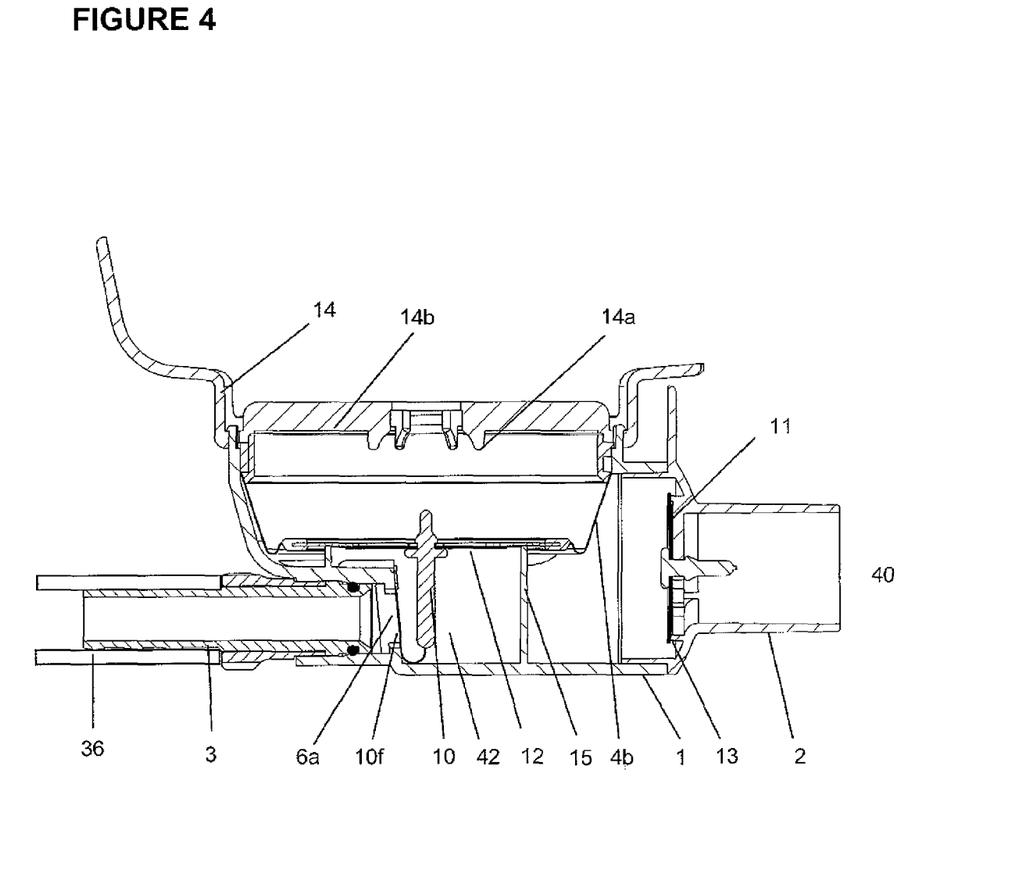
FIGS. 4 to 7 show the third demand valve in each of four operative states.

In one operative state of the demand valve shown in FIG. 4, the demand valve is connected to a vacuum line of for example a hospital waste gas disposal system. In this state, the demand valve closes the vacuum line so power is not drained from the vacuum system. The demand valve can therefore be retained connected to the vacuum line indefinitely or alternatively if an operative omits to disconnect the demand valve from the vacuum line, power in the system is not lost.

In the FIG. 4 state, the inlet 2 may be ready for connection or connected to an exhalation line 40 of a breathing apparatus of a patient. If the inlet 2 is not yet connected to an exhalation line, as indicated above, vacuum power is not drained from the system because the seal 10 closes the seat. If the outlet is connected to an exhalation line, and insufficient flow of exhalation gases enters the housing, the seal remains in position closing the seat. Insufficient flow of exhalation gases occurs when the patient is inhaling, pausing between inhaling stages and exhaling stages or at the beginning or end of exhalation. Typically, sufficient flow of gases occurs almost instantaneously as the pressure in the housing is increased to about +0.5 mbarg. The speed of response is dependent on the weight of the diaphragm, particularly the stiff portion, and if the diaphragm is kept light, then any inertial delay in movement is not noticeable in a typical exhalation curve.

Figure 5:
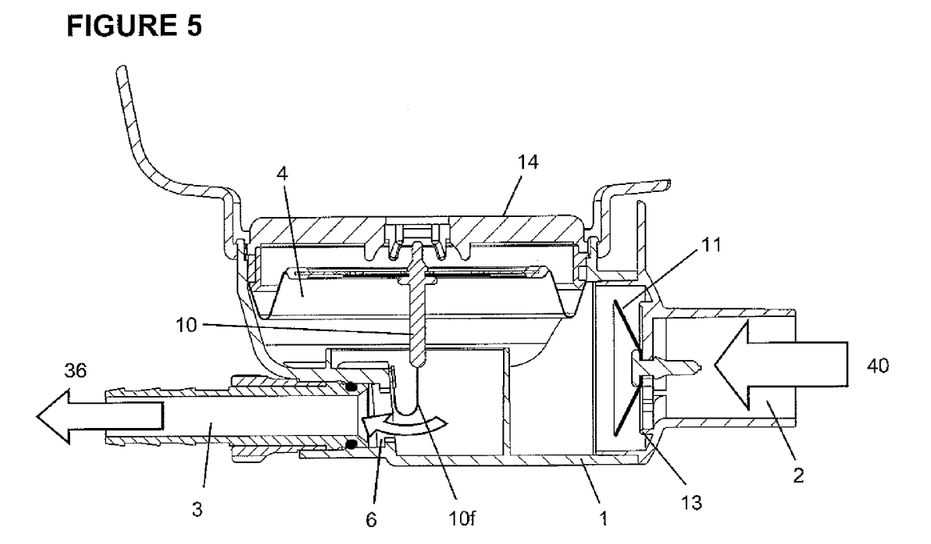

The operative state in FIG. 5 shows the demand valve in conditions of normal exhalation. Exhalation gases passing along the exhalation line 40 cause flap valve 11 to bend against its internal bias generally forming a dish shape providing a space for flow between the outer radial portion of the flap and the seat 13 of the valve. The internal bias is preferably selected so that the valve opens easily at a pressure which is substantially less than the pressure required to open the seal 10. Exhalation gases are therefore allowed to flow into the housing increasing the pressure in the housing.

The pressure in the housing in region 42 acts mainly on the rigid portion of the diaphragm and to a lesser extent on the flexible skirt and the joint between the flexible skirt and the rigid portion. The resultant force on the diaphragm due to sufficient pressure in the housing (e.g. at about 0.001 bar) causes the diaphragm to more in an upwards direction. When the pressure is at or just above 1.001 mbar the diaphragm peels, or rolls, the seal 10 thereby partly opening the apertures in the seat 6. Since the force required to open the seal partly is less than the force required to open the seal fully, the size of the diaphragm may be reduced as compared to the previous embodiments of the invention, particularly the embodiment in FIGS. 1a and 1b. As the patient continues to exhale, the diaphragm lifts higher, causing the seal to be opened more fully to balance the flow entering the housing, and maintain the pressure in the housing at the level needed for the diaphragm to keep the seal open, about +0.5 mbarg. The demand valve is configured such that the seal is opened fully at or a margin above the maximum expected exhalation flow during a breathing cycle of a patient.

Accordingly, the present arrangement has two advantages. Firstly, the size of the diaphragm may be reduced. Secondly, the amount by which the seal is opened is generally commensurate with the exhalation pressure of the patient. Therefore, when more exhalation gases require exhausting to the vacuum system, higher vacuum sucks gas from the housing, and when less exhalation gases require exhausting to the vacuum system, lower vacuum sucks gas from the housing. In this way, high vacuum is not inadvertently connected to the patient which may cause injury or discomfort. Further, power in the vacuum system is not consumed when it is not needed.

In an alternative arrangement the seat 6 and the sealing portion 10f may be horizontal when the seal closes the seat (i.e. perpendicular to the direction of movement of the diaphragm). However, it is preferred that the plane of seat 6 is parallel to the direction of movement of the diaphragm to improve the peeling force for peeling the seal 10 away from the seat and so that the shaft 10g of the seal is in line with the direction of movement. In this regard, if the seal and seat were horizontal, the seal shaft would be required to swing through an angle from a seat open position to a seat closed position.

It has been indicated above that a typical exhalation pressure in region 42 for initially opening the seat apertures is about +0.5 mbarg. Such a pressure allows opening of the seat without significant resistance to exhalation. The pressure of exhalation gases during the breathing cycle of a patient will vary from below atmosphere during inhalation to around +0.5 to 1 mbarg at the peak of exhalation. The breathing cycle varies from one patient to another patient and therefore it is desirable to set the opening pressure and fully open pressure for an average person of highest anticipated size and weight. A deep breathing adult patient exhales peak flows of about 100 liters per minute. Accordingly, the size of the seat 6, when fully open must be such that the pressure in the vacuum line is sufficient to draw more than this into the vacuum line.

Figure 6:
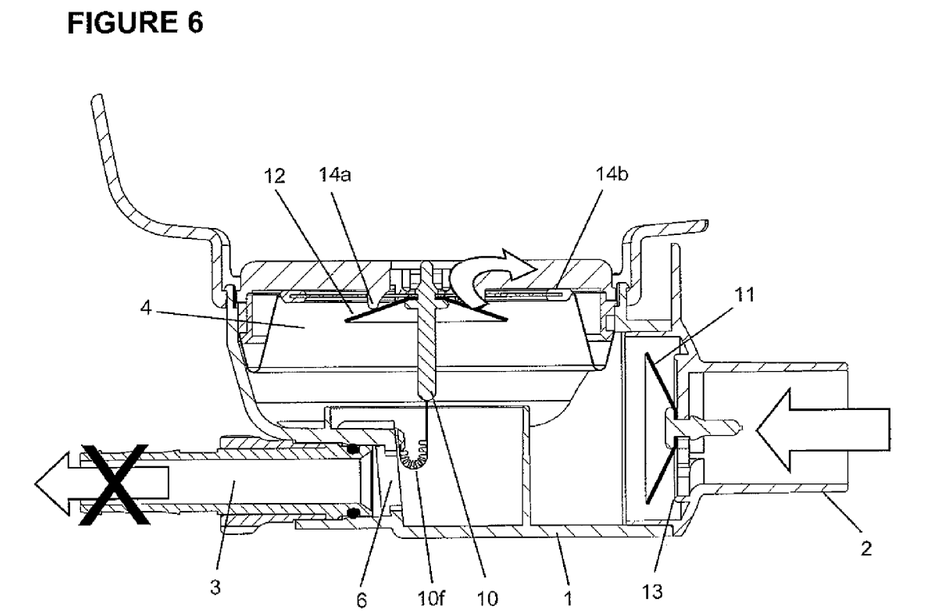

Another state of the demand valve 50 is shown in FIG. 6. In FIG. 6, exhalation occurs, but there is no or insufficient vacuum flow through vacuum line 36 because of for example a blockage in the line or overloading of the vacuum system. Alternatively, the vacuum flow may be acceptable but the patient may cough causing a larger than typical exhalation flow. The demand valve 50 is configured to handle these adverse circumstances without causing harm or discomfort to the patient.

As shown in FIG. 6, the flap valve 11 is opened by exhalation gases and in this example the vacuum line is blocked so that no vacuum flow can occur. As exhalation gases are not sucked away through vacuum line 36, the pressure in the region 42 of the housing continues to increase forcing the diaphragm in an upwards direction. The excess pressure in the housing causes the diaphragm to rise beyond the state in which the seat 6 is fully open. Movement of the diaphragm in this way brings the flap valve 12 into contact with the cover projections 14a which bend the flap valve against its internal bias causing a space to open between the outer portion of the flap valve and the rigid portion of the diaphragm. When flap valve is bent in this way, a flow path to atmosphere is opened through apertures 4e, between the cover and the diaphragm (spaced apart by ribs 14b) and through the vents 14c of the cover part 14. Accordingly, when a patient exhales the exhalation gases are exhausted to atmosphere and do not build up in the housing causing resistance to exhalation. Of course, it is not desirable for exhalation gases to be exhausted to atmosphere because these gases may have a deleterious effect on clinicians' long term health. However, it is preferable, in these adverse circumstances to expose clinicians to minor amounts of exhalation gases than for a patient's exhalation to be impeded.

Figure 7:
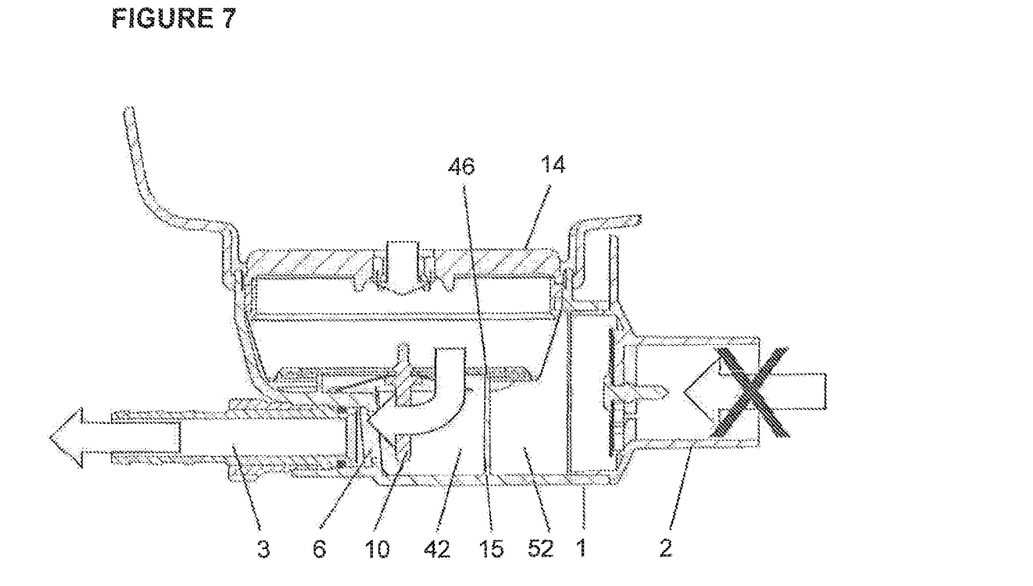

Another state of the demand valve 50 is shown in FIG. 7. Although unlikely, the seal 10 may become defective so that it does not fully close the seat 6 or the seat may be partially open. If the seal becomes defective, the vacuum line will remain open or partially open exposing the patient to vacuum flow even when the patient is not exhaling. As shown in FIG. 7, vacuum flow from the housing causes a reduced pressure in region 42 thereby forcing the diaphragm downwards beyond the position at which the seal would normally be closed. Continued movement of the diaphragm causes it to engage the generally annular wall 15 thereby sealing the outlet 3 (and the vacuum line 36) from the inlet 2 (and the patient) so during inhalation the patient is not exposed to vacuum flow. When the rigid portion engages the wall 15, vacuum flow continues to reduce the pressure in region 42. The pressure differential across the diaphragm in this state causes the flap valve 12 to bend against its internal bias thereby opening apertures 4e in the diaphragm so that gas can flow from atmosphere through vents 14c, between the cover part 14 and the diaphragm (spaced apart by ribs 14b), through diaphragm apertures 4e and into region 42 where it is exhausted through outlet 3 along the vacuum line. When a patient exhales into the housing (not shown in FIG. 7), the pressure in the region of the housing around the wall 15 acts on the rigid portion of the diaphragm causing it to disengage from the wall 15 thereby opening a flow path between the inlet 2 and the outlet so that exhalation gases can be exhausted to the vacuum line.

In the FIG. 7 arrangement, the rigid portion of the diaphragm and the wall 15 are relatively inflexible and not perfectly flat so that a perfect seal between the two parts is not produced. The imperfect seal allows a small amount of leakage which is desirable. In this regard, if the seal were perfect, a slight defect in the rolling seal would cause the diaphragm to be sucked down until seal 12 is opened, increasing the pressure required for the diaphragm to lift on exhalation. In a modification, the wall and/or the rigid portion of the diaphragm may include a relatively small stepped portion through which gas can flow across the wall from region 52 to region 42. Alternatively, the wall may include one or more orifices through which a controlled amount of gas may flow.

The demand valve need not be orientated as shown in the Figures with the cover 14 at the top and housing part 1 at the bottom. The demand valve can work in any orientation since the various pressures required for operation are not dependent on gravity.

Figure 9:
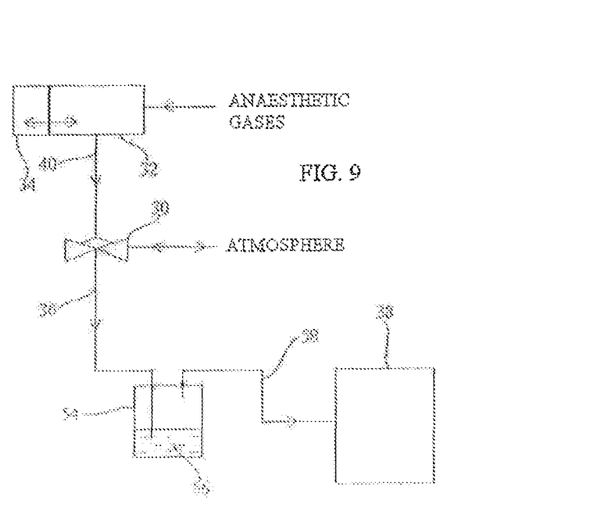
FIG. 9 is a schematic drawing of a breathing apparatus, demand valve, trap and vacuum source.

In a further arrangement shown in FIG. 9, one of the previously described demand valves is connected to the vacuum source 38 through a trap 54. Traps are commonly used to to trap any liquid being drawn into the vacuum line, such as phlegm, blood, aspirate etc. to prevent their entry into the vacuum source along a second vacuum line 58. In more detail, whilst the vacuum source may be maintained approximately at a constant low pressure, the pressure in the conduits and particularly vacuum line 36 connecting to the vacuum source may fluctuate with the flow of gas from the demand valve. Accordingly, the trap comprises a buffer volume which can be reduced in pressure during inhalation by a patient and which can be used to exhaust gas from the demand valve during exhalation. Such an arrangement allows a more constant low pressure in vacuum line 36. The trap may incorporate a filter 56 media which may be of any type selected to trap particulates and liquid droplets that may be sucked into the trap.

In a further arrangement of the demand valve, the housing may be at least partially transparent so that a clinician, for example an anaesthetist, a nurse, or an ODP, can monitor the demand valve in use. The movement of the diaphragm acts as an indicator of a patient's breathing cycle and correct functioning of the demand valve. An internal surface of the transparent part of the housing could have an anti-fog coating to prevent condensation on the transparent surfaces obscuring the vision of the moving parts

The invention claimed is:

1. A vacuum demand valve for use on the exhalation side of a breathing apparatus for controlling a flow of exhalation gases from a patient to a vacuum line, the demand valve comprising:

a housing having a housing inlet which can be connected to an exhalation line of a breathing apparatus to allow exhalation gases to flow into the housing from a patient and a housing outlet which can be connected to a vacuum line to allow gases to flow from the housing into the vacuum line;

a diaphragm having a flexible skirt connected to the housing and a rigid portion supported by the flexible skirt and moveable in response to gas pressure in the housing; and a sealing member connected to the rigid portion of the diaphragm which can engage with the housing outlet to resist a flow of gases from the housing to the vacuum line;

wherein in a first condition of the diaphragm, pressure in the vacuum line causes the sealing member to engage the housing outlet resisting a flow of gases from the housing to the vacuum line and in a second condition of the diaphragm a predetermined pressure of exhalation gases in the housing acts on the rigid portion of the diaphragm causing the sealing member to disengage at least partially from the housing outlet allowing exhalation gases to flow from the housing to the vacuum line; and wherein the sealing member comprises a flexible sealing portion which in the first condition of the diaphragm closes the housing outlet and when pressure in the housing increases above the predetermined pressure due to exhalation, the diaphragm disengages the sealing portion by rolling the sealing portion to open progressively the housing outlet.

2. A vacuum demand valve as claimed in claim 1, wherein the diaphragm remains in the first condition with the housing outlet sealed by the sealing member unless exhalation gases acting on the rigid portion are sufficient to move the diaphragm into the second condition so that the demand valve closes vacuum flow into the vacuum line unless the demand valve is connected to an exhalation line of a breathing apparatus and the apparatus is in use.

3. A vacuum demand valve as claimed in claim 1, wherein movement of the diaphragm is proportional to the pressure of exhalation gases flowing into the housing so that the amount by which the housing outlet is progressively opened is dependent on the amount of exhalation by a patient.

4. A vacuum demand valve as claimed in claim 3, wherein the housing outlet comprises a seat having a plurality of openings therethrough for a flow of gas from the housing to the vacuum line, the sealing portion of the sealing member is formed by a membrane and the seat supports the membrane between the openings and/or the sealing portion comprises strengthening ribs for supporting the membrane.

5. A vacuum demand valve as claimed claim 1, wherein the rigid portion of the diaphragm comprises a plurality of openings therethrough to allow a flow of gas between the housing and atmosphere and the demand valve comprises a valve for selectively sealing the openings in normal operative conditions of the demand valve or opening the openings in adverse operative conditions of the demand valve.

6. A vacuum demand valve as claimed in claim 5, wherein adverse operating conditions comprise a reduction in vacuum pressure in the vacuum line such that vacuum flow into the vacuum line is not sufficient to suck away the exhalation gases in the housing, and wherein the valve opens the openings in the diaphragm to allow exhalation gases to flow to atmosphere.

7. A vacuum demand valve as claimed in claim 5, wherein one or both of the housing and the valve comprise projections which engage with the other of the housing and the valve for opening the openings in the diaphragm when pressure in the housing increases above an upper limit pressure so that exhalation gases can be exhausted to atmosphere from the housing.

8. A vacuum demand valve as claimed in claim 5, wherein adverse operating conditions comprise the sealing member ineffectively sealing the housing opening such that a vacuum flow occurs from the housing to the vacuum line when the diaphragm is in the first condition, and wherein the valve opens the openings in the diaphragm to allow the flow of gas from atmosphere into the housing.

9. A vacuum demand valve as claimed in claim 8, wherein the housing comprises a wall which surrounds the housing outlet and when pressure in the housing is reduced below a lower limit pressure, the diaphragm moves to engage the wall thereby substantially sealing the housing inlet from the housing outlet.

10. A vacuum demand valve as claimed in claim 1, wherein at least a portion of the housing is made from a transparent material so that movement of the diaphragm in use can be observed through the housing.

11. A vacuum demand valve as claimed in claim 1, wherein the housing inlet comprises a one way-valve for resisting a flow of exhalation gases from the housing to the exhalation line.

12. A vacuum demand valve as claimed in claim 1, wherein a patient has a breathing cycle comprising an inhalation stage and an exhalation stage, and wherein the diaphragm is sized such that the predetermined pressure in the housing at which the sealing member opens the housing outlet is exceeded only a short time after the commencement of the exhalation stage to avoid significant resistance to exhalation being applied to the patient by the demand valve.

* * * * *